United States Patent [19]
Donahue

[11] Patent Number: 5,643,303
[45] Date of Patent: Jul. 1, 1997

[54] FLEXIBLE SURGICAL INSTRUMENT

[76] Inventor: John R. Donahue, 530 Rosedale Dr., Pottstown, Pa. 19464

[21] Appl. No.: 662,877

[22] Filed: Jun. 12, 1996

Related U.S. Application Data

[62] Division of Ser. No. 8,918, Jan. 26, 1993, Pat. No. 5,593,416.

[51] Int. Cl.⁶ .................................................. A61B 17/32
[52] U.S. Cl. ........................ 606/170; 606/180; 604/22
[58] Field of Search ................................. 606/159, 170, 606/171, 180; 604/22

[56] References Cited

U.S. PATENT DOCUMENTS

| | | |
|---|---|---|
| 518,600 | 4/1894 | Hallman . |
| 1,636,636 | 7/1927 | Humble . |
| 1,677,337 | 9/1928 | Grove . |
| 3,890,977 | 6/1975 | Wilson . |
| 4,203,444 | 5/1980 | Bonnell et al. . |
| 4,274,414 | 6/1981 | Johnson et al. . |
| 4,646,738 | 3/1987 | Trott . |
| 4,665,906 | 5/1987 | Jervis . |
| 4,705,038 | 11/1987 | Sjostrom et al. . |
| 4,834,729 | 5/1989 | Sjostrom . |
| 4,842,578 | 6/1989 | Johnson et al. . |
| 4,945,920 | 8/1990 | Clossick . |
| 4,983,179 | 1/1991 | Sjostrom . |
| 5,067,957 | 11/1991 | Jervis . |
| 5,152,744 | 10/1992 | Krause et al. . |
| 5,285,795 | 2/1994 | Ryan et al. ............... 606/171 |
| 5,411,514 | 5/1995 | Fucci et al. . |

*Primary Examiner*—Guy V. Tucker
*Assistant Examiner*—William Lewis
*Attorney, Agent, or Firm*—Michael F. Petock, Esq.

[57] ABSTRACT

A flexible surgical instrument is provided which is ideal for providing flexibility in surgery performed through a small incision, such as arthroscopic surgery. In one embodiment, the surgical instrument is provided with an outer member having at least one opening in a distal region and a hollow inner member disposed within the outer member for transmitting force applied to the proximal end to move a cutting implement disposed at the distal end. The cutting implement is constructed and adapted to perform a cutting function at the opening in the outer member. The hollow inner member is substantially flexible between its proximal and distal ends. The outer member is provided with a predetermined flexibility and rigidity such that the outer member is provided with sufficient flexibility to be manually bent by a surgeon during and operation, and provided with sufficient rigidity to retain such bend during the continued performance of the operation with the surgical instrument.

12 Claims, 3 Drawing Sheets

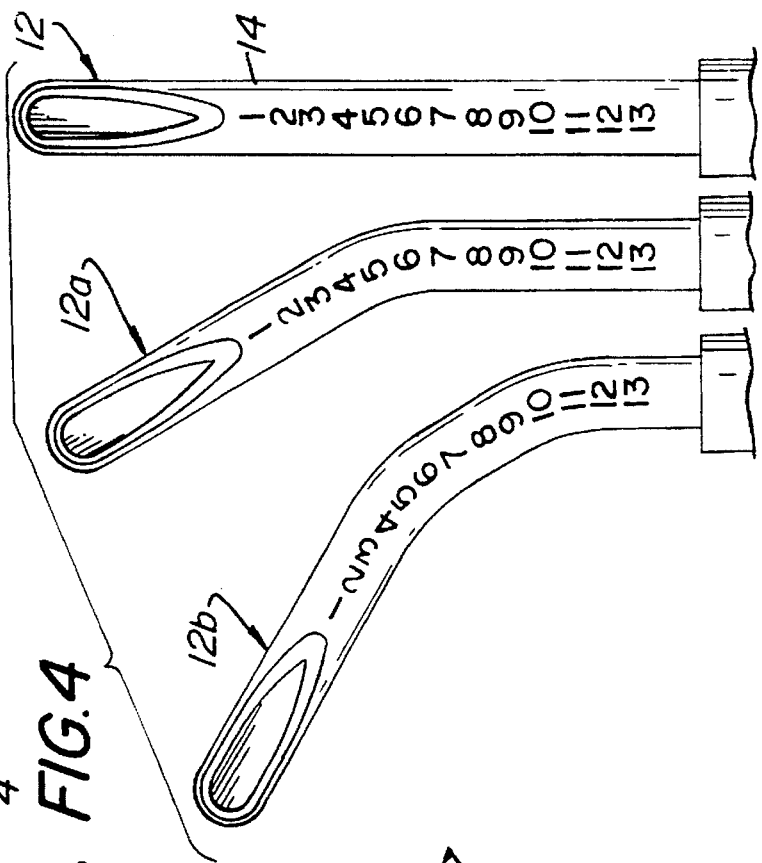
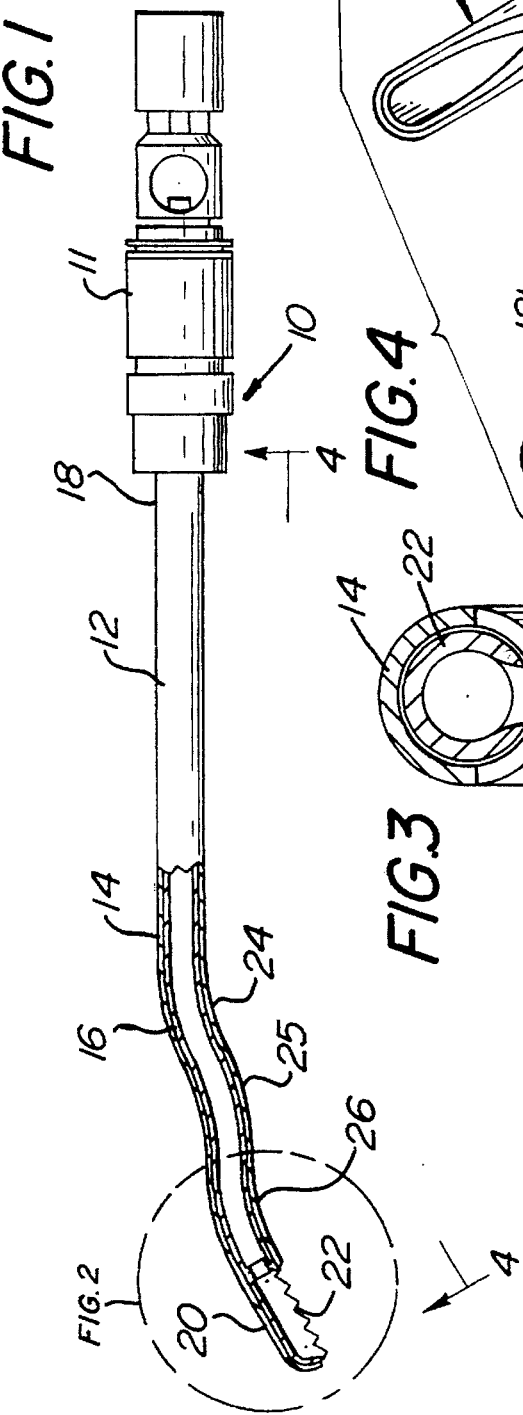
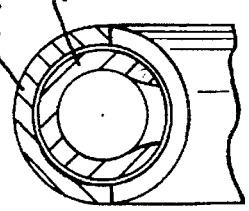
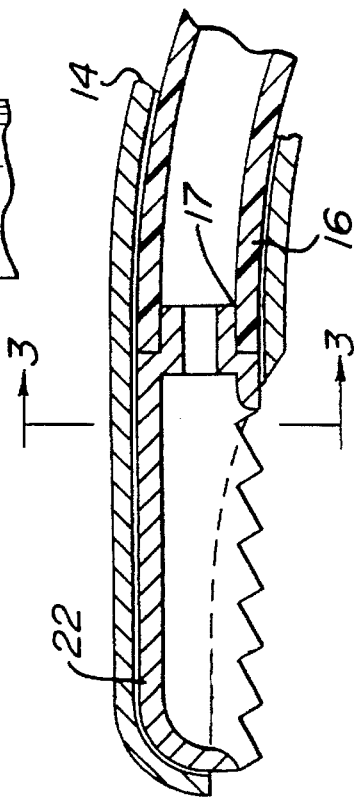

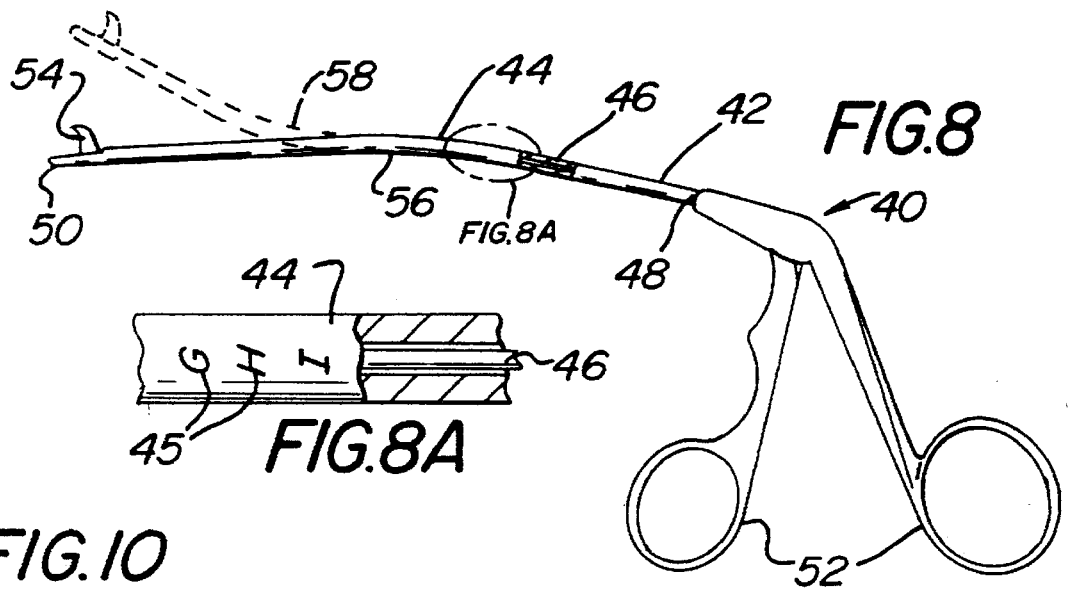
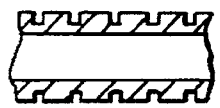
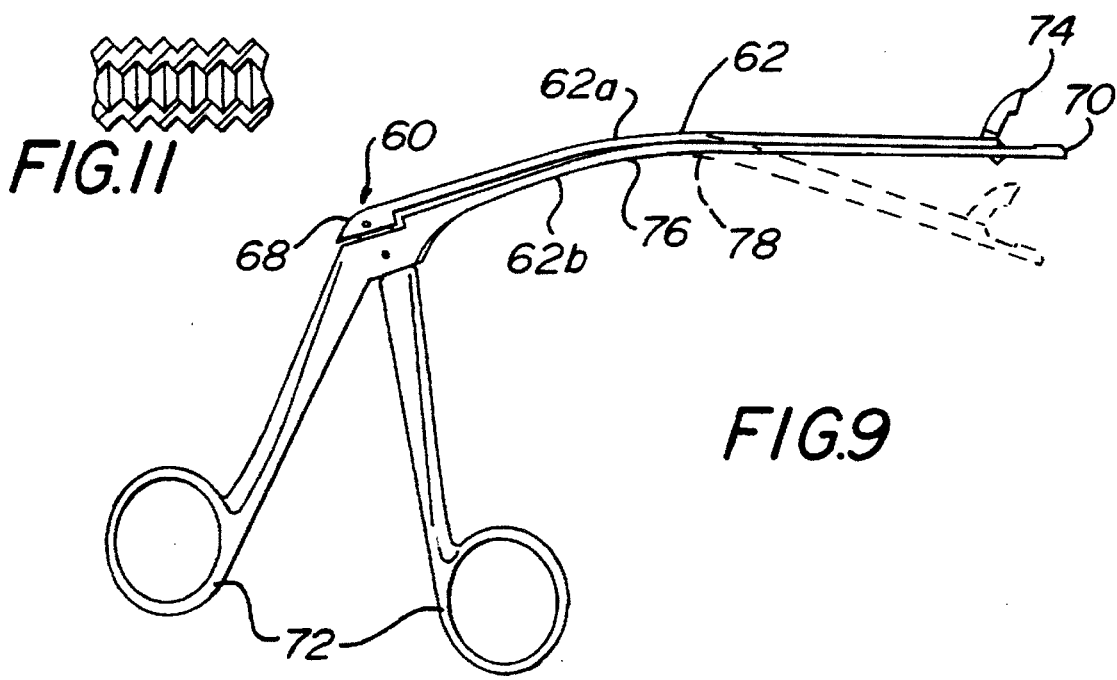

FLEXIBLE SURGICAL INSTRUMENT

CROSS REFERENCE TO RELATED APPLICATION

This application is a division of application No. 08/008,918, filed Jan. 26, 1993, which is now U.S. Pat. No. 5,553,416.

BACKGROUND OF THE INVENTION

This invention relates to a surgical instrument, and in particular to flexible arthroscopic surgical instruments.

Arthroscopic surgical instruments typically include a rigid outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument. Examples of such surgical instruments are described in U.S. Pat. Nos. 4,203,444—Bonnell et al.; 4,274,414—Johnson et al.; and 4,842,578—Johnson et al.

In some instruments, the cutting implement is a hinged jaw mounted at its distal end, and is actuated by hand proximally with the intervening shaft being straight and rigid or rigid with a predetermined bend installed at the time of manufacturing.

The aforesaid typical arthroscopic surgical instruments are linear, or in other words, straight between their proximal and distal ends. Such linear or straight instruments have limitations and disadvantages in many surgical operations, as most body parts and cavities of humans and animals are not straight, but have curved and/or irregular surfaces. It has been recognized that it is sometimes useful for such instruments to be curved to facilitate positioning the cutting implement against the tissue, bone or cartilage to be cut. Accordingly, more recently, arthroscopic surgical instruments have been developed which have a fixed bend or curve placed in the rigid outer tube at the time of fabrication of the instrument. Examples of such instruments with such fixed bends or curves in the rigid outer tube are described in U.S. Pat. Nos. 4,646,738—Trott and 5,152,744—Krause et al. Both of these patents disclose a rigid outer tube with a predetermined bend therein which is placed and fixed in the instrument at the time of fabrication of the instrument. At least a portion of the inner tube for transmitting torque to the cutting blade is made flexible such that it freely rotates within the bend in the outer rigid tube.

SUMMARY OF THE INVENTION

The present invention provides a greater degree of flexibility in the performance of surgical procedures in a body cavity through a small incision. This instrument provides the surgeon with greater flexibility wherein surgical procedures may be performed more easily and more accurately with less discomfort to the patient. This enables the surgeon to more quickly and effectively perform the surgery, and enables more surgical procedures to be performed more effectively under local anesthesia. The instrument provides greater flexibility in any of the surgical procedures now commonly performed through a small incision, such as laparoscopic surgery, gynecological surgery performed vaginally, colonoscopic surgery and particularly arthroscopic surgery where it is often necessary for the instrument to be accurately placed in the curved spaces between the bones of the joint.

In accordance with the method and apparatus of the present invention, greater flexibility is provided to the surgeon by enabling the surgeon to insert the instrument of the present invention into the body cavity, such as a joint, and visualize by means of a scope (such as the arthroscope, which may or may not be connected to a video display) the nature and location of the bend or curve to be placed in the instrument. The surgical instrument is provided with markings on the length of the instrument which enables the surgeon to note the precise location of the desired bends. The surgeon may then remove the instrument, make the necessary bends in the instrument and reinsert the instrument into the body cavity, such as the joint.

Accordingly, in accordance with the present invention, the surgical instrument is constructed for insertion into the body for cutting, wherein it includes an outer member having at least one opening in a distal region. The surgical instrument includes a hollow inner member disposed within the outer member for transmitting force applied to a proximal end to move a cutting implement disposed at the distal end. The cutting implement is constructed and adapted to perform a cutting function at the opening in the outer member. The hollow inner member is flexible between its proximal and distal ends, and the outer member is provided with a predetermined flexibility and rigidity such that the outer member is provided with sufficient flexibility to be manually bent by a surgeon during the operation, and provided with sufficient rigidity to retain such bend during the continued performance of the operation with the surgical instrument.

The method includes the steps of the surgeon inserting the instrument into the body, noting the location of the desired bends by observing the indicia on the outer surface of the outer member, retracting the instrument, performing the bends at the desired location and reinserting the instrument for the continued performance of the surgery.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 1 is a side view, partially broken away in cross-section, of a flexible surgical instrument in accordance with the present invention.

FIG. 2 is an exploded view of the distal end, partially in cross-section, of a flexible surgical instrument in accordance with the present invention.

FIG. 3 is a cross-sectional view taken along line 3—3 of FIG. 2.

FIG. 4 is an elevation view of a flexible surgical instrument initially straight, then with a single bend and then with a double bend therein.

FIG. 8 is a plan view, partially broken away, of a manually operated flexible surgical instrument in accordance with the present invention.

FIG. 8A is an exploded view of the portion of the instrument as indicated in FIG. 8 wherein a portion thereof is shown in cross-section.

FIG. 9 is a plan view of another embodiment of a flexible surgical instrument in accordance with the present invention.

FIG. 10 is a view in cross section of an alternate embodiment of outer tubular member 14.

FIG. 11 is a cross-sectional view of another embodiment of the structure of outer member 14.

DETAILED DESCRIPTION OF THE PREFERRED EMBODIMENTS

Figure 5:
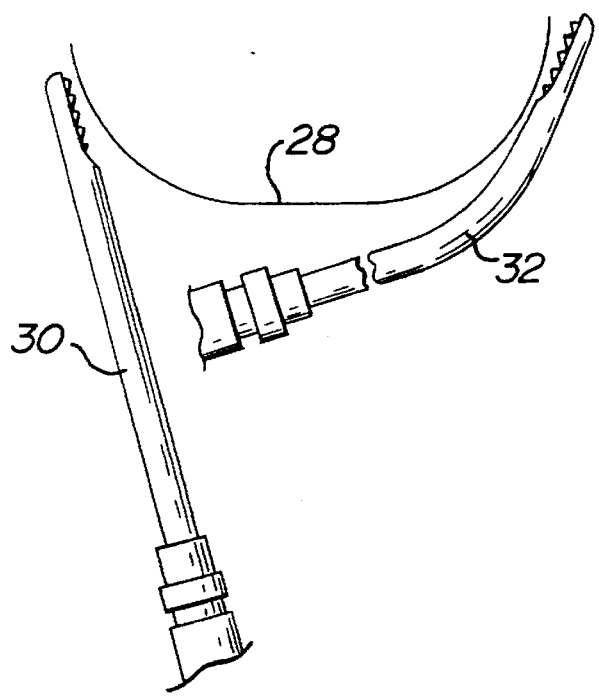
FIG. 5 is an illustration of a side view of two different prior art devices utilized in surgical procedures.

Referring now to the drawings in detail, wherein like numerals indicate like elements, there is shown in FIG. 1 a flexible surgical instrument 10 in accordance with the present invention. The surgical instrument 10 is intended and adapted to be utilized with a hand-held motor unit which is controlled by a foot pedal or other similar switching device which is well known in the field of arthroscopic surgery. For example, a motor and a foot pedal of one suitable type is shown and described in U.S. Pat. No. 4,705,308—Sjostrom et al. The surgical instrument 10 is utilized in surgical procedures such as those which utilize surgical incisions at a joint for a fluid source, a scope connected to a camera and a hand-held motorized unit with a vacuum source, as illustrated and described generally in U.S. Pat. Nos. 4,203,444—Bonnell et al. and 5,152,744—Krause et al. Although a video scope connected to a monitor for use as a video display is generally presently preferred, it is understood that the present invention may be utilized with any type of a scope or viewing device.

The present invention provides the improvement wherein the entire length or substantially the entire length of the portion of the instrument 12 which may be inserted into the body for cutting is provided with a predetermined flexibility and rigidity such that its shape may be adjusted during the surgical procedure by the surgeon with the length 12 retaining this shape, curvature or bend for as long as is desired during the surgical procedure. The portion of the instrument 11, to the right of flexible length 12 in FIG. 1, is adapted to be inserted in or otherwise installed in a hand-held motorized handpiece which has a suction connection of one type conventionally available today. It is understood that the structure of portion 11 may be varied to be received in other types of hand-held motorized units.

The flexible length 12 is comprised of an outer member or outer tube 14 and a hollow inner member or inner tube 16. The inner member 16 is hollow to enable the passage of fluid and tissue that has been cut to be withdrawn from the cutting area by suction or a partial vacuum. As used herein, the term "tissue" is understood to mean broadly all components of the body made up of cells and intercellular material, including not only soft tissue but also cartilage and bone.

Outer member 14 may be constructed of any suitable material which provides sufficient flexibility and rigidity such that outer member 14 may be bent manually by the surgeon during the surgical procedure, and with sufficient rigidity such that the bend placed in outer member 14 is retained during the surgical procedure for so long as desired, with sufficient rigidity to maintain its shape and withstand the forces normally applied to it during such surgical procedures. Outer tube or outer member 14 may be constructed of a titanium alloy or a suitable plastic having memory. Outer member 14 may be ribbed or recessed similar to that shown in FIG. 10, or may be a bellows structure similar to that shown FIG. 11.

The inner member 16 may be constructed of any suitable material which provides sufficient flexibility to enable it to freely rotate within outer member 14, while having sufficient strength to transmit the forces from the proximal end 18 to the distal end 20. Inner member 16 must have flexibility along its length coextensive with the flexibility in outer member 14. Preferably, outer member 14 is flexible along its entire length or substantially its entire length, and accordingly, in a preferred embodiment, inner member 16 would be flexible along its entire length. Inner member 16 may be constructed of any suitable flexible material, such as a flexible plastic, or may be constructed of structures such as those illustrated for a portion of the inner tubular member in U.S. Pat. Nos. 4,646,738—Trott and 5,152,744—Krause et al.

A cutting implement 22 is disposed at the distal end 20 attached to hollow inner member 16 as illustrated in FIG. 2 by any suitable connection. As shown therein, the cutting implement 22 and inner member 16 may be form-fitted and adhesively bonded together at 17.

Referring now to FIG. 4, there is shown an insertable flexible length 12 of an instrument with markings or indicia on its outer surface. The markings shown in FIG. 4 are the numerals 1 through 13. These may be arbitrarily placed on the instrument, or they may represent centimeters of length or other units of measurement. Further, the indicia may be any suitable indicia, including letters or other arbitrary symbols or markings of any type. Markings on the outer surface of outer member 14 are utilized to enable a surgeon to view and identify at what point along the length of insertable instrument the bend should be placed.

As illustrated in FIG. 4, 12 represents a straight insertable length before bending, 12a represents the insertable length wherein a bend has been placed at approximately the location marked between the indicia 5 and 6. In a similar manner, the insertable length 12b illustrates the bend at the location between 5 and 6, and a more rounded bend located approximately at the 10–11 marking. It is understood that bends may be placed at any location along the length 12 as so desired by the surgeon.

Multiple bends of any type or location may be placed in the length of the insertable instrument 12. For example, as illustrated in FIG. 1, there are bends at 24, 25 and 26.

FIG. 5 illustrates two types of prior art instruments being utilized to perform a cutting function at an arcuately shaped bone 28. Instrument 30 is a rigid straight instrument which presents problems, and instrument 32 represents a rigid instrument with a fixed curve, such as that illustrated in U.S. Pat. No. 5,152,744, which again places limitations on the surgical procedure due to the fact that it has a single fixed curve which cannot be adjusted during the surgical procedure.

Figure 6:
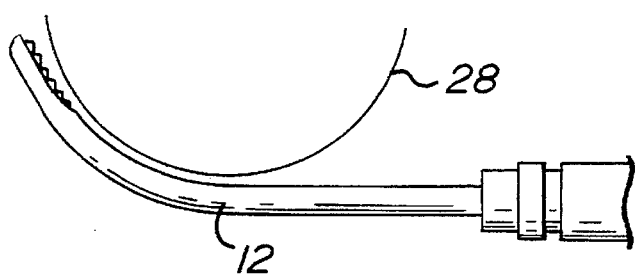
FIG. 6 is a side view of a flexible surgical instrument in accordance with the present invention utilized in a surgical procedure.

Referring now to FIG. 6, there is shown an instrument utilized in accordance with the present invention wherein the outer member 12 may be shaped during the surgical procedure to go around the curved bone 28.

Figure 7:
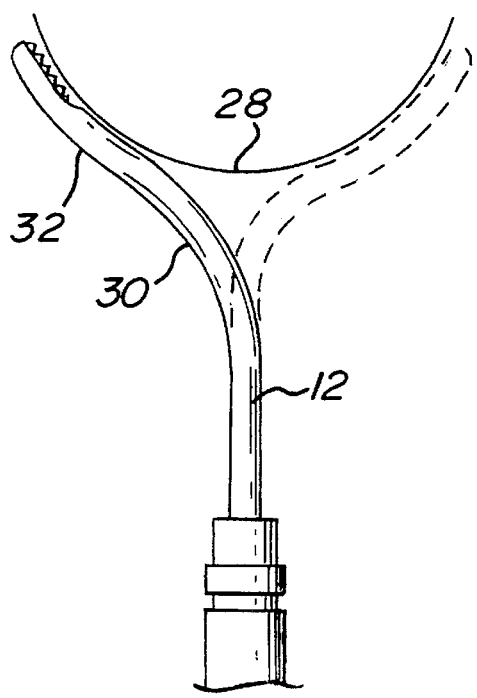
FIG. 7 is a side view of another illustration of the present invention utilized in two different positions in a surgical procedure, one of them being shown in dotted outline form.

FIG. 7 illustrates an implement in accordance with the present invention wherein the instrument may have two oppositely directed curves to enable it to be inserted through a single incision to reach various locations. In FIG. 7, there is a curve at 30 in one direction and a curve in the opposite direction at 32. The curves are of different radii of curvature. The present invention provides ultimate flexibility in shaping or curving the length of instrument 12 to that as desired during the surgical operation. The joints, bones and body cavities of different people are different. Accordingly, no one preset curvature is ideal for all operations on all people and animals. FIG. 7 also illustrates in dotted outline form wherein the instrument may be removed and rotated to access the other side of bone 28 or, alternatively, the instrument may be reshaped.

Referring now to FIGS. 8 and 8A, there is shown a manually operable instrument 40 provided with a flexible length of insertable instrument 42. The outer member or outer tube 44 is provided with a sufficient degree of flexibility between its proximal end 48 and its distal end 50 to enable it to be manually bent or shaped by a surgeon during an operation, and with sufficient rigidity to retain such bend during the continued performance of the operation. As may be seen best in FIG. 8A, within outer member 44 is an inner member 46 which may be a rod which provides the transmission of force between the handles 52 and the cutting implement 54. The inner member 46 may also be a solid or hollow flexible inner member which may transmit the force to cutting implement 54 by rotation.

As illustrated in FIG. 8, instrument 40 is provided with a bend at 56. A second bend is shown in dotted outline form at 58. Any suitable bend may be provided to the instrument shown in FIG. 8. As may be seen in FIG. 8A, the outer surface of outer member 44 may be provided with indicia, such as the letters 45 illustrated in FIG. 8A, or any other suitable markings which may be utilized to aid in viewing the desired location of bends via the scope. The indicia, as stated above, may be numerals or line markings which may or may not be graduated.

Referring now to FIG. 9, there is shown another embodiment of a manually operable instrument 60. Instrument 60 is provided with a length of insertable element 62 which has sufficient flexibility and rigidity such that element 62 may be manually bent by the surgeon during the operation, and has sufficient rigidity to maintain such bend or curvature during the operation for so long as desired. Element 62 is comprised of two slidable elements 62a and 62b. The force is transmitted from handle 72 at the proximal end 68 to cutting implement 74 at distal end 70. As illustrated in FIG. 9, the insertable length 62 is provided with a curve or bend at 76, and another possible bend at 78. The outer surface of member 62 (actually either or beth the outer surfaces of 62a and 62b) may be provided with suitable indicia to aid in locating via the scope the desired location of bends to be placed as described with respect to beth FIGS. 8A and FIG. 4.

The insertable portions 42 and 62 of the instruments of FIGS. 8 and 9 would preferably be supplied without any bends, or in other words, straight. Bends 56 and 58 illustrated in FIG. 8 and bends 76 and 78 illustrated in FIG. 9 are preferably those which may be manually placed into the instrument during the surgical procedure. Alternatively, one or more bends might be provided in the instrument as manufactured.

Although a presently preferred embodiment of the surgical instrument is for the entire insertable portion 12 to be flexible, it is understood that variations may be made wherein less than the entire length of member 12 is flexible. Where less than the entire insertable portion of the instrument is to be made bendable during the surgical procedure, this may be accomplished by either a change in the composition of the material or by the providing of a union wherein a portion of the length is rigid and another portion has the desired degree of flexibility. It will be apparent that other changes and modifications may be made to the surgical instrument within the scope and spirit of the present invention.

In view of the foregoing, the present invention may be embodied in other specific forms without departing from the spirit or essential attributes thereof and, accordingly, reference should be made to the appended claims, rather than to the foregoing specification as indicating the scope of the invention.

I claim:

1. A surgical instrument that is constructed for insertion into a body for cutting, comprising:

an outer member of a predetermined length having at least one opening in a distal region thereof;

a hollow inner member disposed within said outer member for transmitting force applied to a proximal end to rotationally move a cutting implement disposed at a distal end, said cutting implement being constructed and adapted to perform a cutting function at said opening in said outer member; and said hollow inner member being constructed of a flexible plastic and being flexible substantially between its proximal and distal ends, said hollow inner member with said cutting implement attached extending for substantially the entire length of said outer member, and said outer member being provided with a predetermined flexibility and rigidity such that said outer member is provided with sufficient flexibility to be manually bent after manufacture by a surgeon during an operation, and provided with sufficient rigidity to retain such bend during the continued performance of the operation with the surgical instrument wherein said hollow inner member and said outer member are capable of being bent as a unit at any point between said cutting implement and substantially said proximal end.

2. The instrument of claim 1 wherein said outer member is provided with markings on an outer surface of said member extending substantially along its entire length.

3. A surgical instrument that is constructed for insertion into a body for cutting, comprising:

an outer hollow member having at least one opening in a distal region thereof;

an inner hollow member disposed within said outer member for transmitting force applied to a proximal end to move a cutting implement disposed at a distal end, at least a portion of said inner member being flexible, said portion of said inner member being constructed of flexible plastic, said cutting implement being constructed and adapted to perform a cutting function at said opening in said outer member;

a portion of said outer member being provided with a predetermined flexibility and rigidity such that said outer member is provided with sufficient flexibility to be manually bent by a surgeon during an operation, and provided with sufficient rigidity to retain such bend during the continued performance of the operation with the surgical instrument; and the portion of said outer member provided with a predetermined flexibility and rigidity and said flexible portion of said inner member being coextensive.

4. The instrument of claim 3 wherein said inner member is flexible substantially from its proximal end to its distal end and wherein said outer member is provided with said predetermined flexibility and rigidity substantially from said proximal end to said distal end.

5. The instrument of claim 3 wherein said outer member is provided with markings on an outer surface of said member extending substantially along its entire length.

6. A surgical instrument that is constructed for insertion into a body for cutting or grasping, comprising:

an outer member having at least one opening in a distal region thereof;

a flexible inner member disposed within said outer member for transmitting force applied to a proximal end to move a cutting or grasping implement disposed at a distal end, said inner member being constructed of flexible plastic, said implement being constructed and adapted to perform a cutting or grasping function at said opening in said outer member; and said outer member being provided with a predetermined flexibility and rigidity such that said outer member is provided with sufficient flexibility to be manually bent by a surgeon during an operation, and provided with sufficient rigidity to retain such bend during the continued performance of the operation with the surgical instrument.

7. The instrument of claim 6 wherein said outer member is provided with markings on an outer surface of said member extending substantially along its entire length.

8. A surgical instrument that is constructed for insertion into a body for cutting or grasping, comprising:

a first member provided with a cutting or grasping implement disposed in a distal region thereof;

a second member mounted to and slidably movable with respect to said first member, said second member being adapted for transmitting a force applied to a proximal end to move the cutting or grasping implement disposed at a distal end, said implement being constructed and adapted to perform a cutting or grasping function at said distal end; and each of said first and second members being provided with a predetermined flexibility and rigidity such that said first and second members are provided with sufficient flexibility to be manually bent by a surgeon during an operation, and provided with sufficient rigidity to retain such bend during the continued performance of the operation with the surgical instrument.

9. The instrument of claim 8 wherein at least one of said first and second members is provided with markings on a surface of said member extending substantially along its entire length.

10. An endoscopic blade, comprising:

a hollow outer member of a predetermined length having an opening in a distal region thereof;

a rotatable hollow inner member disposed within said outer hollow member for transmitting a rotational force applied to a proximal end to rotationally move a cutting implement disposed at a distal end, said cutting implement being constructed and adapted to perform a cutting function at said opening in said outer member;

said hollow inner member being constructed of a flexible plastic material and being flexible substantially between its proximal and distal ends, said hollow inner member with said cutting implement attached extending for substantially the entire length of said outer member; and said outer member being provided with a predetermined flexibility and rigidity such that said outer member is provided with sufficient flexibility to be bent after manufacture by a surgeon during an operation, and provided with sufficient rigidity to retain such bend during the continued performance of the operation with the surgical instrument wherein said endoscopic blade is capable of being bent at any point between said cutting implement and substantially said proximal end.

11. An endoscopic blade in accordance with claim 10 wherein said hollow outer member is provided with markings on an outer surface of said member.

12. An endoscopic blade in accordance with claim 11 wherein said markings on said outer Surface of said member extend substantially along said hollow outer member from a proximal region to said opening in said distal region.

* * * * *

UNITED STATES PATENT AND TRADEMARK OFFICE
CERTIFICATE OF CORRECTION

PATENT NO. : 5,643,303
DATED : July 1, 1997
INVENTOR(S) : John R. Donahue

It is certified that error appears in the above-indentified patent and that said Letters Patent is hereby corrected as shown below:

Column 5, line 40, delete "beth" and insert -- both --.

Column 8, line 34, delete "S" and insert -- s --.

Title page, item [56], under References Cited--add

| 5,320,635 | 11/17/92 | Smith |
| DE 3,828,478 A1 | 8/22/88 | Kusunoki, et al. |
| EP 0481760 A1 | 4/22/92 | Smith |

Signed and Sealed this

Twenty-third Day of December, 1997

Attest:

BRUCE LEHMAN

Attesting Officer

Commissioner of Patents and Trademarks